US008840951B2

(12) United States Patent
Rijcken et al.

(10) Patent No.: US 8,840,951 B2
(45) Date of Patent: Sep. 23, 2014

(54) METHOD FOR PREPARATION OF A CONTROLLED RELEASE SYSTEM

(75) Inventors: Cristianne Johanna Ferdinand Rijcken, Utrecht (NL); Wilhelmus Everhardus Hennink, Waddinxveen (NL); Cornelis Franciscus Van Nostrum, Vlijmen (NL)

(73) Assignee: Cristal Delivery B.V., Utrecht (NL)

( * ) Notice: Subject to any disclaimer, the term of this patent is extended or adjusted under 35 U.S.C. 154(b) by 333 days.

(21) Appl. No.: 13/119,199

(22) PCT Filed: Sep. 17, 2009

(86) PCT No.: PCT/NL2009/050556
§ 371 (c)(1),
(2), (4) Date: May 5, 2011

(87) PCT Pub. No.: WO2010/033022
PCT Pub. Date: Mar. 25, 2010

(65) Prior Publication Data
US 2011/0217448 A1    Sep. 8, 2011

Related U.S. Application Data

(60) Provisional application No. 61/192,303, filed on Sep. 18, 2008.

(51) Int. Cl.
*A61K 9/28*   (2006.01)
*A61K 9/107*  (2006.01)
*A61K 9/51*   (2006.01)
*A61K 47/48*  (2006.01)

(52) U.S. Cl.
CPC .............. *A61K 9/5138* (2013.01); *A61K 9/1075* (2013.01); *A61K 47/48215* (2013.01); *A61K 47/48169* (2013.01)
USPC ...... 427/2.14; 514/772.1; 424/1.65; 427/2.21

(58) Field of Classification Search
USPC ....................................... 514/772.1; 424/1.65
See application file for complete search history.

(56) References Cited

U.S. PATENT DOCUMENTS

2008/0234391 A1* 9/2008 McCormick et al. ...... 514/772.1
2010/0189643 A1* 7/2010 Chilkoti et al. ............. 424/1.65

FOREIGN PATENT DOCUMENTS

EP           1776400         4/2007
WO    WO 2007/075502 A2    7/2007

OTHER PUBLICATIONS van Nostrum et al., Polymeric Micelles with transient Stability: A Novel Delivery Concept, Feb. 16, 2012, ACS Symposium Series I, pp. 40-56.*

(Continued)

*Primary Examiner* — Dah-Wei D Yuan
*Assistant Examiner* — Andrew Bowman
(74) *Attorney, Agent, or Firm* — Morrison & Foerster LLP

(57) ABSTRACT

The present invention relates to a method for the preparation of a controlled release system and especially to a method for entrapment of compounds in polymer carriers for controlled release of active ingredients, preferably bioactive ingredients, such as drugs. This method results in a system for controlled release of active ingredients and especially for controlled drug delivery. In accordance with the present invention, the tem controlled release" encompasses all kinds of controlled release, including slow release, sustained and delayed release. Particularly, the present invention results in active ingredients, entrapped in or otherwise incorporated in or coupled to polymer carriers or polymeric devices, such as micelles, nanoparticles, microspheres and other types of polymer devices for controlled release; the active ingredients are covalently bonded to the polymer carriers or polymeric devices.

14 Claims, 1 Drawing Sheet

Biodistribution profile and tumour accumulation of free drug, non covalently and covalently entrapped dexamethasone in stabilised polymeric micelles after intravenous administration in mice. Mice were sacrificed after 6, 24 or 48 hours.

(56) References Cited

OTHER PUBLICATIONS

Gallardo et al., "NSAIDs bound to methacrylic carriers: microstructural characterization and in vitro release analysis", Journal of Controlled Release, vol. 71, No. 1, Mar. 12, 2001, pp. 127-140, XP004229500, ISSN: 0168-3659.

PCT Examiner Claudette Cardenas, PCT/NL2009/050556, International Preliminary Report on Patentability, mailed Dec. 3, 2010, 11 pages.

Rijcken et al., "Long circulating biodegradable polymeric micelles: Towards targeted drug delivery", Journal of Controlled Release, vol. 132, No. 3, Dec. 18, 2008, pp. E33-E35, XP025714856, ISSN: 0168-3659.

Rijcken et al., "Methacrylamide-oligolactates as building blocks for targeted biodegradable polymeric micelles to deliver photosensitizers", Journal of Controlled Release, vol. 116, No. 2, Nov. 28, 2006, pp. E10-E12, XP024957716, ISSN: 0168-3659.

Soga et al., "Thermosensitive and biodegradable polymeric micelles for paclitaxel delivery", Journal of Controlled Release, vol. 103, No. 2, Mar. 21, 2005, pp. 341-353, XP004823750 ISSN: 0168-3659.

Bontha et al., "Polymer Micelles with Cross-Linked Ionic Cores for Delivery of Anticancer Drugs," *Journal of Controlled Release* 114, pp. 163-174, 2006.

Davaran et al., "Release of 5-Amino Salicylic Acid from Acrylic Type Polymeric Prodrugs Designed for Colon-Specific Drug Delivery," *Journal of Controlled Release* 58, pp. 279-287, 1999.

Hu et al., "Core Crosslinking of Biodegradable Block Copolymer Micelles Based on Poly(ester carbonate)," *Macromolecular Bioscience* 9, pp. 456-463, 2009.

Kim et al., "Core-Stabilized Polymeric Micelle as Potential Drug Crarrier: Increased Solubilization of Taxol," *Polymers for Advanced Technologies* 10, pp. 647-654, 1999.

Kim et al., "Polymer Micelles with Cross-Linked Polyanion Core for Delivery of a Cationic Drug Doxorubicin," *J. Control Release* 138(3), pp. 197-204, 2009.

Kovar et al., "HPMA Copolymers Containing Doxorubicin Bound by a Proteolytically or Hydrolytically Cleavable Bond: Comparison of Biological Properties in vitro," *Journal of Controlled Release* 99, pp. 301-314, 2004.

Lee et al., "Amphiphilic Poly(D,L-lactic acid)/Poly(ethyleneglycol)/Poly(D,L-lactic acid) Nanogels for Controlled Release of Hydrophobic Drugs," *Macromolecular Bioscience* 6, pp. 846-854, 2006.

Lee et al., "Charge-Conversional Polyionic Complex Micelles—Efficient Nanocarriers for Protein Delivery into Cytoplasm," *Angewandte Chemie* 121, pp. 5413-5416, 2009.

Miyata et al., "Freeze-Dried Formulations for in vivo Gene Delivery of PEGylated Polyplex Micelles with Disulfide Crosslinked Cores to the Liver," *Journal of Controlled Release* 109, pp. 15-23, 2005.

Nakanishi et al., "Development of the Polymer Micelle Carrier System for Doxorubicin," *Journal of Controlled Release* 74, pp. 295-302, 2001.

Nishiyama et al., "Novel Cisplatin-Incorporated Polymeric Micelles Can Eradicate Solid Tumors in Mice," *Cancer Research* 63, pp. 8977-8983, Dec. 15, 2003.

Panarin et al., "Synthesis and Pharmacological Investigation of Water-Soluble Polymeric Derivatives of Glucocorticoids," Khimiko-farmatsevticheskii Zhurnal 23, No. 8, pp. 971-976, 1989.

Rihova et al., "Doxorubicin bound to a HPMA Copolymer Carrier Through Hydrazone bond is Effective Also in a Cancer Cell Line With a Limited content of Lysosomes," *Journal of Controlled Release* 74, pp. 225-232, 2001.

Rijcken et al., "Hydrolysable Core-Crosslinked Thermosensitive Polymeric Micelles: Synthesis, Characterisation and in vivo Studies," *Biomaterials* 28, pp. 5581-5593, 2007.

Ulbrich et al., "HPMA copolymers with pH-controlled release of doxorubicin in vitro cytotoxicity and in vivo antitumor activity," *Journal of Controlled Release* 87, pp. 33-47, 2003.

Rijcken, "Tuneable & degradable polymeric micelles for drug delivery: from synthesis to feasibility in vivo," PhD Thesis, Department of Pharmaceutics, Utrecht University, Utrecht, The Netherlands (2007).

* cited by examiner

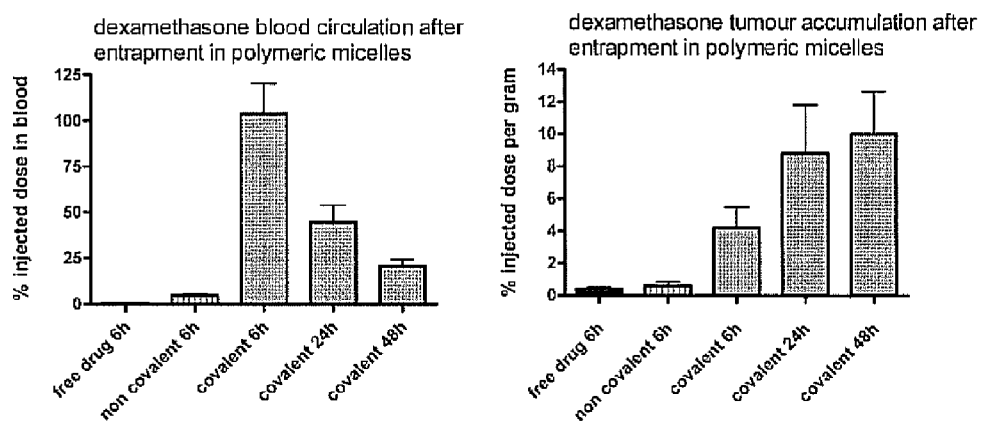
Biodistribution profile and tumour accumulation of free drug, non covalently and covalently entrapped dexamethasone in stabilised polymeric micelles after intravenous administration in mice. Mice were sacrificed after 6, 24 or 48 hours.

METHOD FOR PREPARATION OF A CONTROLLED RELEASE SYSTEM

CROSS REFERENCE TO RELATED APPLICATIONS

This application is a U.S. National Phase Application under 35 U.S.C. §371 of International Application PCT/NL2009/050556, filed on Sep. 17, 2009, which claims the benefit of U.S. Application No. 61/192,303, filed on Sep. 18, 2008, the entire contents of each of which is hereby incorporated by reference in their entireties.

The present invention relates to a method for the preparation of a controlled release system and especially to a method for entrapment of compounds in polymer carriers for controlled release of active ingredients, preferably bioactive ingredients, such as drugs. This method results in a system for controlled release of active ingredients and especially for controlled drug delivery. In accordance with the present invention, the term "controlled release" encompasses all kinds of controlled release, including slow release, sustained and delayed release. Particularly, the present invention results in active ingredients, entrapped in or otherwise incorporated in or coupled to polymer carriers or polymeric devices, such as micelles, nanoparticles, microspheres, hydrogels and other types of polymer carriers or devices for controlled release; the active ingredients are bonded to, and especially covalently bonded to the polymeric devices or carriers.

Nanoparticulate polymeric carriers such as micelles, are considered to be promising candidates for the targeted delivery of drugs. These systems may be constructed so as to have a so-called enhanced permeation and retention effect in a variety of diseased areas. Such polymeric devices for the targeted delivery can contain a broad variety of bioactive ingredients, among which hydrophobic drugs.

In this light, reference can be made to U.S. Pat. No. 7,425,581 and EP-A-1 776 400, describing micelles based on hydrophobically modified PEG-polymethacrylamide block copolymers. These polymers display a unique combination of temperature sensitivity and biodegradability, which provide easy drug loading and controlled release properties, respectively, to the micelles.

Moreover, it was demonstrated by Rijcken et al. in Biomaterials 28 (2007), 5581-5593 that cross-linking of, i.e. the covalent conjugation of, polymers in a micellar core, was essential to realise a long blood circulation of the micelles after intravenous administration in mice. In addition, they found that empty cross-linked micelles accumulate to a 6-fold higher extent in tumour tissue when compared with non-cross-linked micelles.

However, non-covalent (physical) encapsulation of drugs, or other active ingredients, in polymeric micelles (or other devices) often results in the rapid loss of the active ingredients, especially after being applied to the system where the active ingredients are intended to achieve their activity, such as in vivo. This is due to rapid drug diffusion and/or to premature disintegration of the carrier. Although this latter mechanism can be prevented or at least retarded by cross-linking the micelles, the non covalently entrapped drug compounds in these cross-linked micellar cores were prone to burst release immediately after introduction in the human of animal body, such as by intravenous injection. This rapid release from the stabilised micelles is the result of drug diffusion.

In addition, it was found that the properties of the micelles containing non covalently entrapped drugs, as described in said U.S. Pat. No. 7,425,581 and EP-A-1 776 400, are detrimentally affected as a result of aggressive processing, for example freeze-drying. Especially in medical applications and in particular in drug delivery applications, good storage stability of the drug-loaded particles is important. The present invention aims to provide methods for providing long term product stability of drug delivery systems, for instance by lyophilisation (freeze-drying).

In the prior art, methods have been developed for covalent encapsulation of drugs. In covalent encapsulation, active ingredients such as drug molecules are chemically bonded to the polymer chains. These polymers can be hydrophilic and consequently, such systems are termed polymer-drug conjugates that can be administered as such. Alternatively, the polymer can be amphiphilic and in an aqueous environment, micelles are formed which can be administered as such. Such types of micelles may, upon intravenous administration, suffer from stability problems, leading to a disintegration into the separate components. The polymer modification can be done for example by using organic synthesis.

Ulbrich et al. describe in an article in J. Contr. Rel. 87 (2003), 33-47, a water soluble HPMA copolymer conjugated with the anticancer drug doxorubicin. Doxorubicin is attached to the polymer carrier via a hydrolytically labile spacer containing either a hydrazone bond or cis-aconitic acid residue.

Conjugates with hydrolytically-releasable doxorubicin are also described by Ríhová et al. in J. Contr. Rel. 74 (2001), 225-232, and Kovár et al. in J. Contr. Rel. 99 (2004) 301-314.

A polymer micelle carrier system for doxorubicin is described by Nakanishi et al. in J. Contr. Rel. 74 (2001) 295-302. First, doxorubicin is conjugated to a block copolymer of polyethylene glycol and polyaspartic acid. Next, a micelle carrier system is formed by dissolving this modified polymer in an aqueous environment. This carrier system additionally encompasses free (physically entrapped) doxorubicin.

In Panarin et al., Pharmaceutical Chemistry Journal 23, (1989), 689-694, derivatives of glucocorticoids are disclosed which are derivatised with water-soluble polymers. In particular, it is disclosed that hydrocortisone, prednisolone or dexamethasone is acylated by a copolymer of vinylpyrrolidone with maleic anhydride to form polyesters of said glucocorticoids.

Covalent bonding of drug molecules can also be done by the copolymerisation of polymerisable drug derivatives upon polymer synthesis. In Davaran et al., J. Contr. Rel. 58 1999, 279-287, drug-containing monomers are free radically copolymerized with methacrylic acid or hydroxyethyl methacrylate. The acrylic polymer backbone bears the drug units as side substituents attached through hydrolysable bonds, such as ester or amide bonds.

Disadvantages of these known systems are the necessity to perform organic synthesis to couple the drug molecules to high molecular weight polymer chains (with consequent challenges), and the necessity to develop a new polymer for each drug molecule which limits the applicability of a new polymer platform technology. In addition, in polymer-drug conjugates mainly water-soluble polymers are used for covalent bonding of drug molecules, thereby often limiting the application of these polymer-drug conjugates to water-soluble drugs. Moreover, hydrophilic polymer-drug conjugates are less stable in aqueous solution as these remain in contact with the aqueous solution and, thus, easily degrade.

In accordance with the present invention a method is provided wherein the above mentioned disadvantages are overcome. That is, a method is provided wherein active ingredients such as drug molecules are first non-covalently entrapped in polymer phases, and especially in polymer-rich phases, in an aqueous environment, and subsequently are conjugated to a 3D-polymer network.

Particularly, in accordance with the present invention a method was found, for the preparation of a controlled release system comprising a polymer matrix incorporating an active ingredient, said method comprising the steps of:

(i) mixing an active ingredient comprising a reactive moiety with an aqueous solution or dispersion comprising polymer chains comprising at least one reactive moiety, capable of reacting with the reactive moiety of the active ingredient, the polymer chains further being capable of cross-linking intra- or intermolecularly; and (ii) subjecting this mixture to cross-linking forming a polymer matrix under such conditions that simultaneous with the formation of the polymer matrix the active ingredient is entrapped in this polymer matrix, that is in the polymeric network formed. In step (i) the polymer chains preferably interact with each other (see herein-below) forming polymer sub phases in an aqueous phase. That is, relatively, polymer chain-rich and relatively polymer chain-poor phases are created. In the best mode, the active ingredient has a preference to be present in the polymer chain rich phases. A sub-location of active ingredients in polymer chain rich sub-phases occurs based on physical interactions between the active ingredients and the polymer chains. In step (i), the active ingredients do not form covalent conjugates with the polymer chains. Only in cross-linking step (ii) the active ingredients and the polymer chains together form a 3D-network.

The active ingredients are covalently bonded to the polymer carrier simultaneously with the cross-linking of the polymers forming the polymeric carrier or device. The cross-linked active ingredient-polymer conjugates which are formed using the method of the present invention exhibit a higher thermodynamic stability than the non-cross-linked polymer particles. In addition, the entrapped drug molecules are prevented from rapid release due to covalent bonding to the polymeric carrier.

The method of the invention does not require the coupling of drug molecules directly to single polymer chains up-front, thereby fully retaining the initial properties of the polymers used, such as thermo-sensitive properties and/or the ease of drug-loaded micelle formation. The use of a fixed type of polymer, for example thermo-sensitive biodegradable block copolymers, provides a broadly applicable platform technology that allows a rapid and easy change/optimization of the composition of the drug-loaded devices.

The method is applicable to all active ingredients that non-covalently interact with polymer chains that are capable of forming polymeric carriers after cross-linking. In the aqueous phase, the polymer chains (before the cross linking step) preferably assemble in a certain structure, or at least in polymer chain-rich domains; and the active ingredients localise in these assemblies. All types of physical interactions are possible (see below) but in a preferred embodiment, the active ingredients are rather hydrophobic, or at least non-hydrophilic.

The only further requirement is that the active ingredient contains a moiety (or can be modified with a reactive substituent) that is capable to react with a moiety of the polymer chains that form the basis of the polymeric device or carrier.

By covalent entrapment of the drug molecules in the core of the carrier, such as in the micellar core, the drugs will benefit from the prolonged blood circulation of the cross-linked carrier in the body and consequently lead to elevated drug concentrations in tumour tissue, and in this way the present invention has advantages over the above cited U.S. Pat. No. 7,425,581 and EP-A-1 776 400.

In addition, the products prepared by the method of the present invention may obtain a long term product stability by subjecting these to lyophilisation. For example, drug-loaded micelles prepared according to the method of the invention can easily be freeze-dried and subsequently resuspended without loss of morphology; as dry powder, a long shelf life is obtained.

Hence, the present invention concerns a method for the non covalent entrapment of (drug) molecules in polymeric carriers in an aqueous environment, whereby the polymer chains of the polymeric carrier contain at least one reactive moiety. This non covalent entrapment is followed by a simultaneous crosslinking reaction between the optionally, yet generally, modified (drug) molecules and the polymer chains, thereby forming an intertwined network.

The resulting drug-loaded polymeric devices, such as micelles, do not display a premature release of active ingredient, but demonstrate a prolonged blood circulation. This results for instance in a (greatly) enhanced tumour accumulation When the drug is entrapped via a degradable linker, a constant release of the therapeutically active compound is assured. Controlled release of the (drug) molecules from the carrier is accomplished by cleavage of the, preferably degradable, linker or linking group between the active ingredient, such as a drug molecule, and the polymeric carrier under physiological conditions, or by local environmental triggers or external stimuli as explained and elaborated, herein-below. In addition, the encapsulation prevents exposure of blood to toxic high drug peak levels that would otherwise be present immediately after intravenous administrations of free drugs. More importantly, by preventing migration of the drug to normal tissues, acute toxic effects may be diminished. The other way around, the (drug) molecules are fully protected from the environment by confinement in the formed three-dimensional network of the cross-linked polymer carrier, such as a cross-linked micellar core, thereby preventing a premature degradation and/or clearance. These unique aspects deliver the drug at the right place and time, and at an anticipated efficacious dose.

The stepwise method of the invention comprises two essential consecutive steps.

In the first step, a cross-linkable polymer and an active ingredient are mixed in an aqueous environment. This is preferably achieved by adding the active ingredient, optionally in a suitable solvent that preferably is water or a water miscible solvent such as a lower alcohol like ethanol, or tetrahydrofuran, to an aqueous polymer solution or dispersion. The polymer present and the active ingredient are selected so that the polymer and the active ingredient will be in intimate contact, and in a preferred embodiment, the active ingredient has a preference to be in contact with the polymer chains. Said in other words, in the first step physical, non covalent interactions between the polymer chains and the active ingredient result in the selective localisation of compounds in specific regions of a polymeric device.

As a result of the first step, the molecules forming the active ingredients are non-covalently entrapped in and between the polymer chains in solution. In the present description and the appending claims, the concept of "non-covalent interaction" means any interaction which is not covalent, i.e. any weak bonding between atoms or bonds which bonding does not involve the sharing of electron pairs. Examples of non-covalent interaction are hydrophobic, aromatic, hydrogen bonding, electrostatic, stereocomplex, and metal-ion interactions.

In the second essential step of the method of the invention, the non-covalently entrapped active ingredients are covalently coupled to the newly forming/formed polymer network. That is, a reaction is carried out, wherein the polymer chains are cross-linked. This can occur both inter- and intramolecularly, but the intermolecular cross-links are clearly preferred and any steps that favour intermolecular cross-linking are preferred embodiments of the presently claimed process. Simultaneously with the cross-linking step, the reactive moieties of the active ingredients are also co-crosslinking and an intertwined network of the polymers and the active ingredients is formed.

Often, this step requires initiators, but also physical circumstances may lead to the reactions forming cross-links and conjugates. In case initiators are required, these may be added to the polymer solution together with the active ingredient, but can also added to the reaction system at an earlier or later stage.

Suitable amounts of active ingredients are amounts of 0.1-30 wt. %, preferably 0.5-15 wt. %, such as amounts of 1-10 wt. % drawn to the weight of polymer+active ingredients. Since the degree of incorporation of active ingredient may be as high as 95-100%, similar amounts may be incorporated in the formed 3D-network.

According to a preferred method of the present invention, amphiphilic polymers may be fully dissolved in a solvent;

(bio)active compounds may be present in the solvent or may be added after the dissolution of said polymers, and the (bio)active compounds will form a general distribution over the polymer solution;

then, this system may be subjected to a change of certain circumstances (e.g. temperature, pH, solvent) leading to a situation that at least parts of the polymers display a different behaviour than other parts of the polymers and clustering takes place;

due to the physical properties of the (bio)active agents, these agents localise in certain regions of the newly formed clustered polymeric solution;

after this localisation, cross-linking takes place to fixate the (bio)active compounds in their preferred regions.

In a preferred embodiment of the method of the invention, thermosensitive block copolymers are used. For example, the active ingredient is mixed in an aqueous environment, wherein also a non-cross-linked thermosensitive block copolymer is present at a temperature lower than its Lower Critical Solution Temperature (LCST) or lower than its critical micelle formation temperature (CMT). At any temperature below this LCST, the system is in solution; at any temperature below this CMT, micelle formation does not occur. However, by heating such systems, particles or micelles are formed thereby entrapping active hydrophobic ingredients in their hydrophobic core. Next, the cross-linking reaction that forms the intertwined micellar network in the core is also carried out at a temperature higher than the LCST or the CMT. This cross-linking reaction can be accelerated by the addition of an initiator, either prior to heating of the polymer solution or after formation of the non-cross-linked particles or micelles.

Suitable polymer chains that can be used in the present invention are, e.g., thermo-sensitive block copolymers. Particularly, copolymers based on PEG-b-poly(N-hydroxyalkyl methacrylamide-oligolactates) with partially methacrylated oligolactate units are preferred. Various other (meth)acrylamide esters can be used to construct the thermosensitive block, e.g. esters, and preferably (oligo)lactate esters, of HPMAm (hydroxypropyl methacrylamide) or HEMAm (hydroxyethylmethacrylamide), and N-(meth)acryloyl amino acid esters. Preferred thermo-sensitive block copolymers are derived from monomers containing functional groups which may be modified by methacrylate groups, such as HPMAm-lactate polymers.

Other types of functional thermosensitive (co)polymers, which can be used, are hydrophobically modified poly(N-hydroxyalkyl)(meth)acrylamides, copolymer compositions of N-isopropylacrylamide (NIPAAm) with monomers containing reactive functional groups (e.g., acidic acrylamides and other moieties such as N-acryloxysuccinimide) or similar copolymers of poly(alkyl) 2-oxazalines, etc.

Further preferred thermo sensitive groups can be based on NIPAAm and/or alkyl-2-oxaxolines, which monomers may be reacted with monomers containing a reactive functional group such as (meth)acrylamides or (meth)acrylates containing hydroxyl, carboxyl, amine or succinimide groups.

Suitable thermo-sensitive polymers are described in U.S. Pat. No. 7,425,581 and in EP-A-1 776 400.

However, also other types of amphiphilic block copolymers or ionic micelles that are not necessarily thermo-sensitive and contain or can be modified with cross-linkable reactive groups, may be used. In such cases state-of-the-art methods can be used to form the micelles, such as direct dissolution, dialysis, and solvent-evaporation.

These other types of polymers that conform polymer-rich phases in water (e.g. due to hydrophobic interactions or ionic interactions) and that contain reactive moieties or contain moieties that can be used to couple reactive moieties, e.g. PEG-PLA-methacrylate (e.g. as described in detail in Kim et al., Polym. Adv. Technol., 10 (1999), 647-654), methacrylated PLA-PEG-PLA (e.g. as described by Lee et al. in Macromol. Biosci. 6 (2006) 846-854), methacrylated PEG-poly caprolactone (e.g. as described by Hu et al. in Macromol. Biosci. 9 (2009), 456-463), as well as other reactive moieties containing (block co)polymers based on poly lactic acid, poly lactic acid glycolic acid, and/or poly caprolactones.

In addition, polymers capable of forming micelles because of ionic interactions may be used, such as block ionomer complexes of poly (ethylene oxide)-b-poly (methacrylic acid copolymers and divalent metal cations (e.g. as described by Kim et al. in J. Control. Rel. 138 (2009) 197-204, and by Bontha et al. in J. Control. Rel. 114 (2006) 163-174) polyionic complexes based on block copolymers of poly (ethylene glycol) and poly (amino acid) (e.g. as taught in Lee et al., Angew. Chem 121 (2009) 5413-4516; in Nishi yama et al. in Cancer Res. 63 (2003), 8977-8983, or in Miyata et al., J. Control. Rel. 109 (2005) 15-23.

In general, all polymers that are able to create different subphases in a suitable solvent system can be used, together with (bio)active agents that can localize selectively in such subphases.

Active ingredients to be entrapped in the polymers, include but are not limited to, drug molecules, peptides/proteins, imaging agents, genetic material or a combination of these compounds. Preferably, these active ingredients should be of a nature such that these tend to interact in a physical non-covalent manner with the polymer chains of the polymers described herein-above. In a preferred embodiment and when using the thermosensitive polymers, the invention is especially useful for encapsulation of hydrophobic compounds. Good results are obtained with active ingredients having a logP higher than 1, preferably higher than 2. For the definition of logP reference is made to Chemical Reviews 1971, volume 71, number 6.

The polymer chains and the active ingredients contain or may be modified such that these contain reactive and/or polymerisable moieties, and especially free-radical polymerisable moieties, including but not limited to, terminal double bonds (e.g., vinyl groups, (meth)acrylate, (meth)acrylamide), and unsaturated compounds (e.g., linear chains containing carbon-carbon double bonds). It goes without saying that the active ingredient is selected or modified such that the free-radical initiation only leads to a bond formed from the reactive group. This guarantees that the active ingredient maintains its desired effects in the intended end-use application.

The polymers used should contain a sufficiently high number of reactive substituents capable of cross-linking and reacting with the reactive groups of the active ingredients. Suitable results are obtained when for instance 10-15% of the monomer units of the polymer have a reactive substituent; however also up to 100% of the monomer units may be derivatised with reactive substituents.

The release rate of the active ingredients can easily be controlled by using different type of linkers to conjugate the reactive moiety to the active ingredients. Suitable types of well-known degradable linker molecules include but are not limited to esters, carbonates, carbamates, succinate or ortho esters, ketals, acetals, hydrazone, and enzymatically degradable linkers (e.g. peptides) or a combination of these. In addition, all kinds of well known stimuli sensitive linkers, such as photo-/temperature-/ultrasound-sensitive and other linkers can also be used. When modifying bioactive ingredients, one takes care of the type of conjugation such that upon release, only the original molecule is released and no derivatives, as to assure its therapeutic activity. By using a biodegradable linkage, the original active ingredient, such as a drug molecule, will be released according to a specific controlled release profile and subsequently exert its activity and especially its therapeutic effect.

The products obtained by the method of the present invention are polymer carriers, such as micelles, nanoparticles, microspheres, hydrogels and other types of polymer carriers or devices comprising entrapped or otherwise incorporated active ingredients for controlled release, such as devices with a coating with entrapped active ingredients.

As said, in the second essential step of the method of the invention, cross-linking and conjugation is effected. Thereto, one may use several types of (free radical) initiators for polymerisation induced cross-linking, including but not limited to, KPS (potassium persulphate)/TEMED, photo-initiators, thermo labile initiators, redox initiators, and metal ligands for ring opening metathesis polymerisation. Also living free radical polymerization techniques may be employed (for example Atom Transfer Radical Polymerisation (ATRP) and Reversible Addition Fragmentation chain Transfer (RAFT). Dependent on the end-use application of the encapsulated active ingredients, the residues of the initiators may be removed by repeated washing or by other known techniques.

By way of example, the formation of a specific embodiment of the method of the present invention is described. In this embodiment, one starts from copolymers based on PEG-b-poly(N-hydroxyalkyl methacrylamide-oligolactates) with partially methacrylated oligolactate units. Hydrophobic (drug) molecules are derivatised with a polymerisable moiety that is attached to the drug molecule via a degradable linker, such as a carbamate ester. An aqueous solution of said thermo-sensitive block copolymers is subsequently mixed with a small amount of a concentrated solution (typically 10:1 volume ratio) of (slightly) hydrophobic drug molecules in a water-miscible organic solvent (preferably with a low boiling temperature e.g. ethanol or tetrahydrofuran) at a temperature below the polymers CMT, i.e. that does not allow micelle formation. Then, an initiator solution (KPS-TEMED) is added, immediately followed by rapid heating till above the critical micelle formation temperature (CMT). This results in the formation of monodisperse polymeric micelles (size around 70 nm) where the (drug) compounds are non covalently localised in the hydrophobic core via hydrophobic interactions. After micelle formation, a nitrogen atmosphere is created. Thereby, the initiator radicals will induce polymerisation of the methacrylated polymers and the polymerisable drug compounds having a reactive moiety. This cross-linking process results in the formation of an intertwined network and fixates the drug covalently inside the micellar core, without affecting the micellar size or uniformity.

Thus, (drug) molecules are covalently entrapped in the cross-linked micelles. The micelles in this embodiment swell in a physiological environment by hydration after (partial) hydrolysis of the unmodified oligolactate units, whereafter the drug is released upon cleavage of the degradable linker. This cleavage can also be the result of local environmental triggers or external stimuli.

The method of the invention is not limited to the use of polymers that can form micelles. It also allows for the non covalent entrapment and subsequent covalent cross-linking of (drug) molecules in polymeric nanoparticles, microspheres, hydrogels or coatings. With regard to the application of these devices containing (drug) compounds, the present invention encompasses the following non-limiting embodiments:

(a) controlled release of (drug) molecules entrapped in the cross-linked micelles upon administration in vivo, e.g. by oral application, injection in the blood stream, or by direct injection in an organ or tumour;

(b) controlled release of drug and/or proteins entrapped in a cross-linked polymeric microspheres or a hydrogel upon localised administration; and (c) controlled release of (drug) molecules upon coating of a device with entrapped drug molecules, such as by dual spraying of ice cold aqueous polymer solution and drug solution (in organic solvent) onto a medical device which is kept above the phase transition temperature of the thermo-sensitive polymer. After the subsequent cross linking and the evaporation of solvents, a cross linked coating is formed.

The invention will be now illustrated by the following, non limiting example.

EXAMPLE

In this example, dexamethasone was chosen as model drug compound because of its dual mechanism of action, i.e. the down-regulation of pro-inflammatory cytokines and pro-oncogenic signals. Consequently, dexamethasone is extensively used as anti-inflammatory agent and recently, a significant antitumour effect of corticosteroids after tumour targeted delivery was confirmed.

Particularly, $^3$H-dexamethasone was modified with a methacrylate unit via a degradable carbamate ester linker, and $^{14}$C-labelled polymer was used to follow the pharmacokinetics and biodistribution of the drug and the carrier independently by means of liquid scintillation counting of blood and tissue samples. The modified dexamethasone was physically entrapped by the above described specific embodiment based on PEG-b-poly(N-2-hydroxypropyl methacrylamide-oligolactate) with partially methacrylated oligolactate units (CMT of 11° C.), and subsequently, covalently attached to the cross-linked micellar core. Free drug, or non covalently or covalently entrapped dexamethasone in crosslinked polymeric micelles were intravenously administered in B16F10 tumour-bearing mice which were sacrificed after 6, 24 or 48 hours. The results are depicted in FIG. 1, which shows the biodistribution profile and tumour accumulation of free drug, non covalently entrapped dexamethasone and covalently entrapped dexamethasone in micelles after intravenous administration to mice, these mice being sacrificed after 6, 24 of 48 hours.

The non-covalent entrapment of unmodified dexamethasone in cross-linked micelles did not prolong the drug's blood circulation. However, in case of the covalently entrapped dexamethasone, more than 95% of the covalently drug-loaded micelles still resided in the blood stream after 6 hours as compared to 0.3% of free dexamethasone. Besides, ten percent of the injected dose of covalently bonded dexamethasone accumulated per gram of a subcutaneous tumour, which is a 23-fold increase as compared to free dexamethasone. Ultimately, the biodegradability of the linker between the drug and the micelles governs the therapeutic activity of the entrapped drug.

The invention claimed is:

1. A method for the preparation of a controlled release system which is a three-dimensionally cross-linked polymer network comprising active ingredient molecules covalently coupled through a linker to and entrapped in said three-dimensionally cross-linked polymer network, the method comprising the steps of:
   (i) mixing under conditions that do not result in cross-linking
      (a) active ingredient molecules coupled through said linker to a polymerisable moiety with
      (b) an aqueous solution or dispersion comprising polymer chains, said polymer chains forming a non-cross-linked matrix and comprising polymerisable moieties that will polymerise under cross-linking conditions with the polymerisable moiety linked to the active ingredient molecules to entrap the active ingredient molecules within the polymer matrix,
   the polymer chains comprising polymerisable moieties that will result in cross-linking intra- or intermolecularly under cross-linking conditions
   thus non-covalently entrapping said active ingredient molecules in the non-cross-linked polymer matrix; and
   (ii) subjecting this mixture to cross-linking conditions, thereby forming a three-dimensionally cross-linked polymer network simultaneously with covalently coupling the molecules of the active ingredient both to the polymer network and to other active ingredient molecules included in said network;
   wherein said cross-linking conditions include a polymerisation initiator and wherein the controlled release system of polymer chains and active ingredient molecules is stabilized.

2. The method of claim 1, wherein the polymer chains are thermosensitive polymer chains.

3. The method of claim 2, wherein in step (i) the active ingredient molecules are mixed in the aqueous solution or dispersion comprising the non-cross-linked polymer chains initially at a temperature lower than the Lower Critical Solution Temperature (LCST), after which step (ii) is carried out at a temperature higher than the LCST; or
   wherein in step (i) the active ingredient molecules are mixed in the aqueous solution or dispersion, comprising the non-cross-linked polymer chains initially present at a temperature lower than the Critical Micelle Formation Temperature (CMT), after which step (ii) is carried out at a temperature higher than the CMT.

4. The method of claim 2, wherein the thermosensitive polymer chains are selected from (co)polymers containing hydrophobically modified esters of N-hydroxyalkyl-(meth)acrylamide or N-(meth)acryloyl amino acids.

5. The method of claim 2, wherein the polymer chains contain functional groups that are methacrylated.

6. The method of claim 2, wherein thermosensitive polymers chains include monomers derived from N-isopropylacrylamide and/or alkyl-2-oxazolines.

7. The method of claim 2, using micelle, hydrogel microparticle and/or coating-forming polymers containing said thermosensitive polymer chains.

8. The method of claim 7, which are di- or triblock copolymers with PEG.

9. The method of claim 1, wherein the active ingredient is a drug molecule, a peptide, a protein, an imaging agent, genetic material or a combination of these compounds.

10. The method of claim 1, wherein the polymerisable moieties comprise C=C double bonds.

11. The method of claim 1 wherein the polymerisable moiety is coupled to the active ingredient molecule through a biodegradable linker.

12. The method of claim 5 wherein the polymer chains comprise (co)polymers of N-hydroxyalkyl methacrylamide-oligolactates.

13. The method of claim 10 wherein the polymerisable moieties comprise vinyl groups, (meth)acrylate groups, or (meth)acrylamide groups.

14. The method of claim 1 wherein the polymerization initiator is a free radical initiator.

* * * * *